(12) United States Patent
Vautz et al.

(10) Patent No.: US 9,874,578 B2
(45) Date of Patent: Jan. 23, 2018

(54) APPARATUS FOR TAKING A SAMPLE AND FOR PASSING THE SAMPLE TO AN ANALYTICAL EVALUATION SYSTEM

(71) Applicant: Leibniz-Institut fuer Analytische Wissenschaften-ISAS-e.V., Dortmund (DE)

(72) Inventors: Wolfgang Vautz, Unna (DE); Peter Roeper, Dortmund (DE); Luzia Seifert, Dortmund (DE)

(73) Assignee: Leibniz-Institut fuer Analytische Wissenschaften-ISAS-e.V., Dortmund (DE)

( * ) Notice: Subject to any disclaimer, the term of this patent is extended or adjusted under 35 U.S.C. 154(b) by 277 days.

(21) Appl. No.: 14/806,954

(22) Filed: Jul. 23, 2015

(65) Prior Publication Data
US 2016/0025762 A1    Jan. 28, 2016

(30) Foreign Application Priority Data

Jul. 25, 2014   (DE) .................... 10 2014 110 544

(51) Int. Cl.
*G01N 35/10*    (2006.01)
*G01N 1/20*    (2006.01)
(Continued)

(52) U.S. Cl.
CPC .......... *G01N 35/10* (2013.01); *G01N 1/2035* (2013.01); *G01N 1/2247* (2013.01); *G01N 1/24* (2013.01);
(Continued)

(58) Field of Classification Search
CPC ..................................................... G01N 35/10
See application file for complete search history.

(56) References Cited

U.S. PATENT DOCUMENTS 2,388,662 A   11/1945   Anderson et al.
5,087,319 A   2/1992   Held
(Continued)

FOREIGN PATENT DOCUMENTS

DE   39 20 946 A1   1/1991
DE   41 25 141 C2   8/1993
(Continued)

*Primary Examiner* — Paul West
*Assistant Examiner* — Mark A Shabman
(74) *Attorney, Agent, or Firm* — Collard & Roe, P.C.

(57) ABSTRACT

An apparatus for taking a sample from at least one fluid system and for passing the sample to an analytical evaluation system connects the piston rod of the sample-taking piston with a controllable drive. A flushing gas feed opens into a feed line downstream from a three-way valve, via a shut-off valve. The three-way valve, the controllable drive, and the shut-off valve are coupled with one another so that for taking a sample, the three-way valve releases the path of the sampling line to the sample-taking cylinder, the shut-off valve is open, and the controllable drive withdraws the sample-taking piston from the sample-taking cylinder, and, for applying the sample to the evaluation system, the shut-off valve is closed, the three-way valve is switched to release the path from the sample-taking piston to the feed line, and the controllable drive pushes the sample-taking piston completely back into the sample-taking cylinder.

10 Claims, 2 Drawing Sheets

(51) Int. Cl.
    *G01N 1/22*        (2006.01)
    *G01N 1/24*        (2006.01)
    *G01N 1/14*        (2006.01)

(52) U.S. Cl.
    CPC ............... *G01N 2001/1427* (2013.01); *G01N 2001/205* (2013.01); *G01N 2001/247* (2013.01)

(56) References Cited

U.S. PATENT DOCUMENTS

| | | | |
|---|---|---|---|
| 5,088,335 A | | 2/1992 | Lafreniere et al. |
| 5,221,477 A | * | 6/1993 | Melcher ............ B01D 11/0415 210/198.2 |
| 5,375,478 A | | 12/1994 | Bernhardt |
| 5,717,131 A | * | 2/1998 | Sunde .................... G01N 11/08 166/270 |
| 5,736,654 A | | 4/1998 | Dubois |
| 6,419,127 B1 | | 7/2002 | Fershtut |
| 7,690,245 B2 | | 4/2010 | Jung |
| 2002/0106804 A1 | * | 8/2002 | Tanaka ................... G01N 35/10 436/54 |
| 2007/0144274 A1 | * | 6/2007 | Gibson ................ G01N 1/2035 73/863.02 |

FOREIGN PATENT DOCUMENTS

| | | |
|---|---|---|
| DE | 199 37 026 A1 | 8/2000 |
| DE | 10 2004 004 342 A1 | 8/2005 |
| DE | 100 61 725 B4 | 5/2009 |
| EP | 0 022 654 A1 | 1/1981 |

\* cited by examiner

APPARATUS FOR TAKING A SAMPLE AND FOR PASSING THE SAMPLE TO AN ANALYTICAL EVALUATION SYSTEM

CROSS REFERENCE TO RELATED APPLICATIONS

Applicant claims priority under 35 U.S.C. §119 of German Application No. 10 2014 110 544.3 filed Jul. 25, 2014, the disclosure of which is incorporated by reference.

BACKGROUND OF THE INVENTION

1. Field of the Invention

The invention relates to an apparatus for taking a sample from at least one fluid system and for passing the at least one sample taken to an analytical evaluation system.

2. Description of the Related Art

An apparatus for taking a sample from at least one fluid system and for passing the at least one sample taken to an analytical evaluation system, having at least one sample-taking cylinder with a sample-taking piston guided on it is known from DE 39 20 946 C2.

DE 10 2004 004 342 A1, U.S. Pat. Nos. 5,088,335 A, 5,717,131 A, 6,419,127 B1, DE 100 61 725 B4, U.S. Pat. No. 2,388,662 A, DE 41 25 141 C2, DE 199 37 026 A1, EP 0 022 654 A1, and U.S. Pat. No. 5,736,654 A show various further apparatuses for taking fluid samples.

Taking fluid samples from a gaseous or liquid fluid system, which can involve a flowing or stationary volume, and subsequently passing the samples to an analytical evaluation system, for example a mass spectrometer or an ion mobility spectrometer, preferably with prior separation (for example by means of gas chromatography, liquid chromatography or electrophoresis), is of great importance for many applications, for example process control, diagnostics from respiratory air, head space analysis and many more.

For this purpose, in the simplest case, a fluid sample is taken from the fluid system using a syringe or the like, concentrated if necessary, and transported to a laboratory, where it is transferred to an analysis system. This method of procedure is time-consuming and cost-intensive; the analysis result is often available only with a clear time delay (hours to days). For this reason, quasi on-line methods are increasingly being used. For example, a sample from a volume or volume stream is drawn into a sample volume using a pump, for example, and this volume is then injected into the pre-separation unit of the analysis system by means of a carrier flow. It is true that such a method is clearly faster, but it requires flushing the sample volume for an appropriate period of time, in order to displace the previously existing volume, as well as flushing the sample volume into the pre-separation unit. This corresponds, in principle, to exponential dilution of the sample (flushing out a high initial concentration, which leads to an exponential decrease in concentration) during injection, with the result that the signals are delayed or, if the flushing-in process is broken off, a loss of part of the sample occurs after a certain period of time.

SUMMARY OF THE INVENTION

It is the task of the invention to create a solution with which rapid sample-taking from a fluid system is guaranteed, without a flushing process of the sample volume, along with fast and loss-free injection of the sample into the analytical evaluation system.

This task is accomplished by means of an apparatus in accordance with the invention for taking a sample from at least one fluid system and for passing the at least one sample taken to an analytical evaluation system having at least one sample-taking cylinder with a sample-taking piston guided in it. An opening of the sample-taking cylinder is connected with a first connector of a three-way valve, the second connector of the three-way valve is connected with the fluid system by way of a sampling line, and the third connector of the three-way valve is connected with the evaluation system by way of a feed line. The piston rod of the sample-taking piston is connected with a controllable drive, and a flushing gas feed opens into the feed line downstream from the three-way valve, by way of a shut-off valve.

In this connection, the method of functioning of the apparatus is as follows:

The three-way valve, the controllable drive, and the shut-off valve are coupled with one another so that for taking a sample, the three-way valve releases the path of the sampling line from the fluid system to the sample-taking cylinder, the shut-off valve for the flushing gas feed is open, and the controllable drive pulls the piston out of the cylinder so that the sample-taking cylinder acts in the manner of a syringe and draws the sample out of the fluid system into the sample-taking cylinder. After the sample-taking cylinder has been filled, the shut-off valve is closed to apply the sample to the analytical evaluation system, the multi-way valve is switched so that the path from the sample-taking piston to the feed line is released, and that the controllable drive pushes the sample-taking piston completely back into the sample-taking cylinder, thereby causing the sample to be conveyed into the analytical evaluation system.

In this manner, the time for taking the sample and passing the same to the analytical evaluation system clearly takes less than 1 second in every case, in some cases actually only a few milliseconds, depending on the design and size of the sample-taking cylinder and sample-taking piston. In this connection, the entire sample volume is pressed into the analytical evaluation system or its pre-separation unit in an extremely short period of time, as a packet, so to speak, so that as compared with conventional flushing-in with a carrier gas, a higher maximal concentration is guaranteed, with the better detection strength connected with it. Furthermore, tailing is also reduced, in other words the peak width of the signals at half height during the retention time is reduced, and thereby better separation with greater selectivity is achieved.

In a particularly preferred embodiment, the controllable drive is configured as a piston/cylinder unit, the piston rod of which is connected with the piston rod of the sample-taking piston, wherein the cylinder of the piston/cylinder unit has a pressure medium connector on both sides of the piston, in each instance, which connector is connected with a pressure medium source by way of a common three-way valve, in each instance. During sample-taking, the three-way valve is then switched in such a manner that the specific pressure medium connector of the piston that causes the piston to be moved in the direction opposite to the sample-taking piston is connected with the pressure medium source; for sample-taking, the path from the pressure medium source to the other pressure medium connector is released by way of the three-way valve, so that the piston is moved in the direction toward the sample-taking piston and thereby the sample is pressed into the analytical evaluation system.

This embodiment of the controllable drive is particularly preferred and allows extremely rapid taking of a sample and passing the same on to the analytical evaluation system.

Furthermore, the apparatus effort and the control effort are very low, because only two three-way valves and one shut-off valve (one-way valve) are required.

In this connection, conventional compressed air, for example, which is usually available, in any case, can be used as a pressure medium source. In this connection, the consumption of compressed air is very slight and is not important.

In this connection, the piston of the piston/cylinder unit and the sample-taking piston preferably have a common piston rod.

Alternatively, the controllable drive can also be structured differently, for example as an electrically activated piston or the like.

It is also possible to modify the apparatus in such a manner that multiple sample volumes are operated in parallel, by means of one or more pneumatic pistons, for example for simultaneous alternating sample-taking, (damp) flushing, and drying.

For this purpose, it is provided that multiple sample-taking cylinders are provided with sample-taking pistons, which are each connected with a separate fluid system and the feed line by way of their own three-way valve.

Alternatively, it can be provided that the sample-taking cylinder with sample-taking piston is connected with multiple fluid systems and the feed line, by way of a multi-way valve.

BRIEF DESCRIPTION OF THE DRAWINGS

Further characteristics, details, and advantages of the invention are evident from the following description and using the drawings. The exemplary embodiments of the invention are shown purely schematically in the following drawings, and will be described in greater detail below. Objects or elements that correspond to one another are provided with the same reference symbols in all the figures.

In the drawings.

DETAILED DESCRIPTION OF THE PREFERRED EMBODIMENTS

Figure 1:
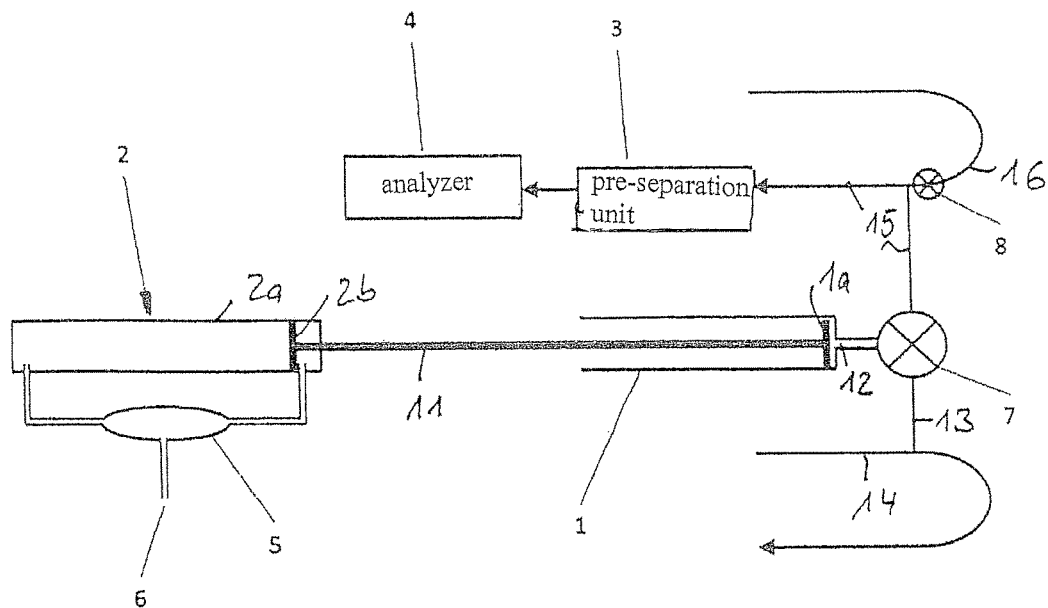
FIG. 1 shows the fundamental structure of the apparatus, with indicated fluid systems and analytical evaluation system.

An apparatus according to the invention, for taking a sample from at least one fluid system 14 (for example a gaseous or liquid flowing or stationary volume) and for passing the sample taken to an analytical evaluation system, which, in the exemplary embodiment, has a pre-separation unit 3, for example by means of gas chromatography, liquid chromatography, electrophoresis, or the like, and an analyzer 4 (for example a mass spectrometer or ion mobility spectrometer), first has a sample-taking cylinder 1, in the exemplary embodiment, with a sample-taking piston 1a guided within it. A piston rod 11 of the sample-taking cylinder 1a is connected with a controllable drive. This controllable drive is configured, in the exemplary embodiment, as a piston/cylinder unit 2, which has a cylinder 2a and a piston 2b. In this connection, in the exemplary embodiment, the piston rod of the piston 2b is the piston rod 11 of the piston 1a, i.e. both the sample-taking piston 1a and the piston 2b have a common piston rod 11 and are disposed, in each instance, at opposite ends of the piston rod 11. The cylinder 2a of the piston/cylinder unit 2 has a pressure medium connector 9, 10 on both sides of the piston 2b, i.e. at the front and rear end of the cylinder 2a, in each instance, which connector is connected with a pressure medium source 6 by way of a common three-way valve 5, in each instance.

The sample-taking cylinder 1 has an opening 12 that faces away from the piston rod 11, which opening is connected with a first connector of a three-way valve 7. The second connector of the three-way valve 7 is connected with the fluid system 14 by way of a sampling line 13, and the third connector of the three-way valve 7 is connected with the pre-separation unit 3 of the analytical evaluation system by way of a feed line 15.

Downstream from the three-way valve 7, the feed line 15 opens into a flushing gas feed indicated with 16, by way of a shut-off valve 8 (one-way valve).

Figure 2:
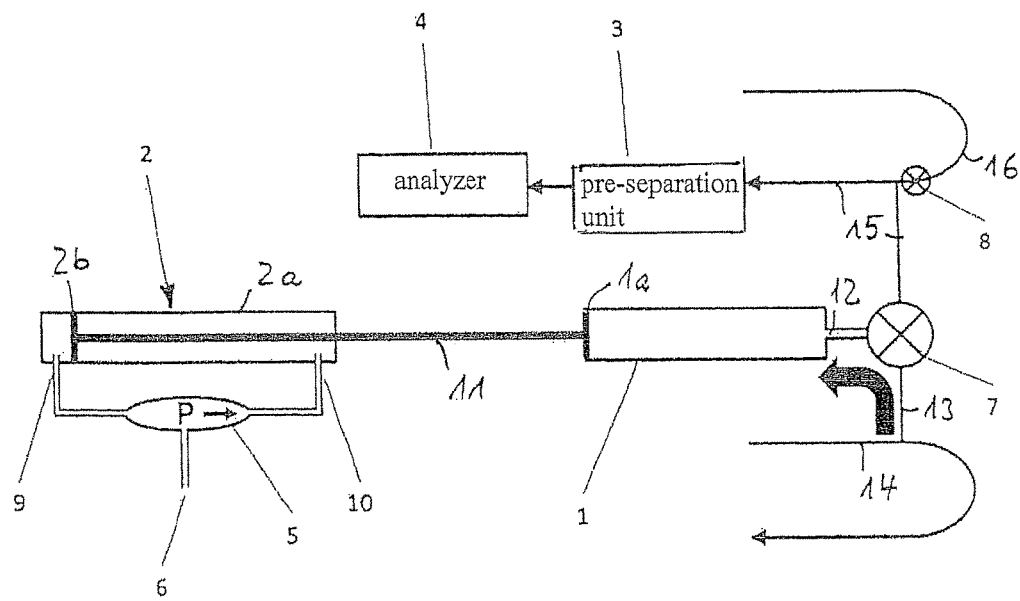
FIG. 2 shows the apparatus according to FIG. 1 during sample-taking.

The method of functioning of the apparatus is as follows:

For taking a sample from the fluid system 14, the position of the valves is as follows, as shown in FIG. 2:

The shut-off valve 8 is open, so that flushing gas is flushed into the pre-separation unit 3. The three-way valve 7 is switched in such a manner that the path between the sampling line 13 and the opening 12 of the sample-taking cylinder 1 is open. Finally, the three-way valve 5 is switched in such a manner that the path from the pressure medium source 6 to the pressure medium connector 10 of the cylinder 2a of the piston/cylinder unit 2 is free, thereby causing the piston 2b to be moved to the left in the sense of FIG. 2, by means of the pressure medium entry into the cylinder 2a, i.e. the piston rod 11 also moves to the left, and accordingly, so does the sample-taking piston 1a in the sample-taking cylinder 1. As a result, a sample is drawn into the sample-taking cylinder 1, which acts like a syringe, out of the fluid system 14 through the open sampling line 13.

In the end position shown in FIG. 2, the sample-taking cylinder 1 is therefore completely filled with a sample.

Figure 3:
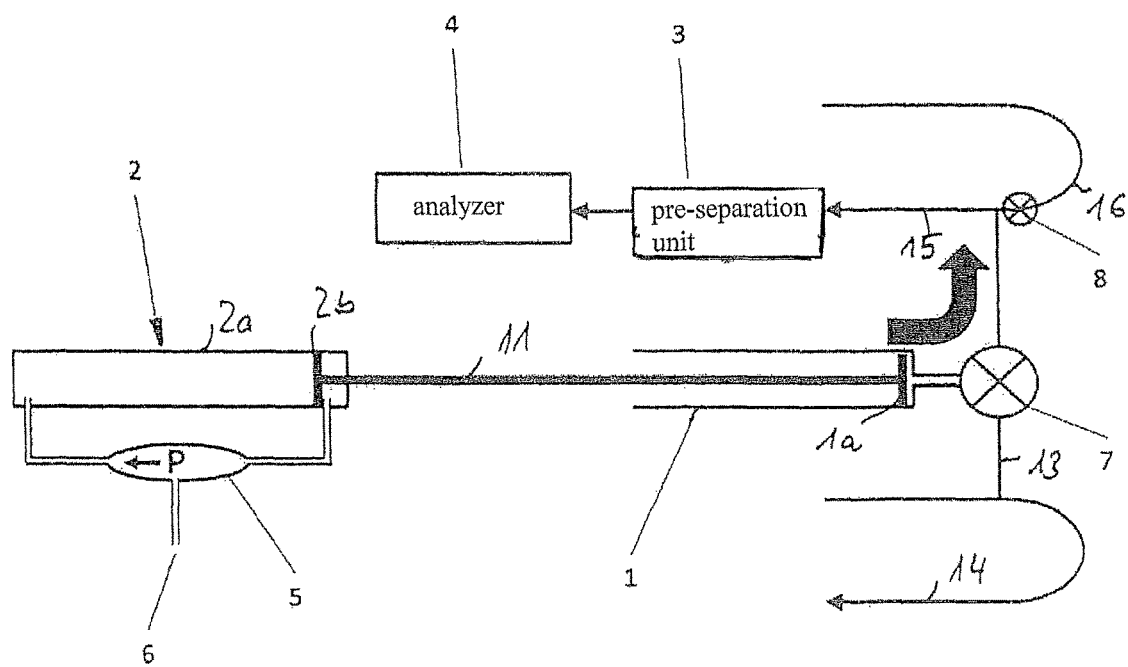
FIG. 3 shows the apparatus according to FIGS. 1 and 2 during feed of the sample into the evaluation system.

Subsequently, the three valves 8, 7, and 5 are simultaneously switched to a different position, the shut-off valve 8 is closed, so that no flushing gas can get into the feed line 15 any more; at the same time, the three-way valve 7 releases the path from the opening 12 to the feed line 15 and the three-way valve 5 releases the path from the pressure medium source 6 to the pressure medium connector 9. As a result, as shown in FIG. 3, the piston 2b of the piston/cylinder unit 2 moves to the right and simultaneously presses the piston 1a into the sample-taking cylinder 1, thereby pressing the sample situated in the sample taking cylinder to be pressed into the pre-separation unit 3 through the feed line 15, and subsequently into the analyzer 4.

In this manner, sample-taking and sample application as a whole takes clearly less than 1 second, possibly actually only a few milliseconds, depending on the design and size of the piston/cylinder unit 2 and of the sample-taking piston 1 and the applied pressure of the pressure medium source 6.

Of course, the invention is not restricted to the exemplary embodiment shown. Further embodiments are possible without departing from the basic idea. For example, the controllable drive can also be structured in a different way, for example as an electric drive for the piston rod 11 of the sample-taking piston 1a. Furthermore, it is also possible to modify the apparatus in such a manner that multiple sample volumes are operated in parallel, by means of one or more sample-taking cylinder(s) 1 and sample-taking piston(s) 1a.

Thus, although only a few embodiments of the present invention have been shown and described, it is to be understood that many changes and modifications may be made thereunto without departing from the spirit and scope of the invention.

What is claimed is:

1. An apparatus comprising:
    (a) at least one fluid system;
    (b) at least one analytical evaluation system;
    (c) at least one sample-taking cylinder having an opening;
    (d) a sample-taking piston guided in the at least one sample-taking cylinder and comprising a first piston rod;
    (e) a three-way valve having a first connector connected with the opening, a second connector connected by way of a sampling line to the at least one fluid system, and a third connector connected by way of a feed line with the analytical evaluation system;
    (f) a controllable drive connected with the first piston rod, wherein the first piston rod is movable in both directions by the controllable drive;
    (g) a shut-off valve; and
    (h) a flushing gas feed opening into the feed line downstream from the three-way valve by way of the shut-off valve;
    wherein the three-way valve, the controllable drive, and the shut-off valve are coupled with one another in such a manner that:
        in a first position of the apparatus for taking a sample from the at least one fluid system, the three-way valve releases a path of the sampling line to the at least one sample-taking cylinder, the shut-off valve is open, and the controllable drive pulls the sample-taking piston out of the at least one sample-taking cylinder for suctioning-up the sample in the sample-taking cylinder; and
        in a second position of the apparatus for applying the sample to the analytical evaluation system, the shut-off valve is closed, the three-way valve is switched in such a manner that a path of the sample-taking piston to the feed line is released, and the controllable drive pushes the sample-taking piston again completely back into the at least one sample-taking cylinder for conveyance of the sample into the analytical evaluation system.

2. The apparatus according to claim 1, wherein
    the controllable drive is configured as a piston/cylinder unit comprising a piston, a cylinder and a second piston rod connected with the first piston rod of the sample-taking piston, wherein the cylinder of the piston/cylinder unit has first and second pressure medium connectors on first and second sides of the piston, respectively, wherein each connector is connected with a pressure medium source by way of a common three-way valve.

3. The apparatus according to claim 1, wherein the controllable drive is configured as a piston/cylinder unit comprising a piston and a cylinder and wherein the first piston rod serves as a common piston rod for the piston of the piston/cylinder unit and the sample-taking piston.

4. The apparatus according to claim 1, wherein a plurality of sample-taking cylinders and a plurality of sample-taking pistons guided in the sample-taking cylinders are provided, wherein each sample-taking piston is connected with a separate fluid system and the feed line by way of a separate three-way valve.

5. The apparatus according to claim 1, wherein the at least one sample-taking cylinder and the sample-taking piston guided in the at least one sample-taking cylinder are connected with a plurality of fluid systems and the feed line by way of a multi-way valve.

6. A method comprising:
    (a) providing an apparatus comprising at least one fluid system; at least one analytical evaluation system; at least one sample-taking cylinder having an opening; a sample-taking piston guided in the at least one sample-taking cylinder and comprising a first piston rod; a three-way valve having a first connector connected with the opening, a second connector connected by way of a sampling line to the at least one fluid system, and a third connector connected by way of a feed line with the analytical evaluation system; a controllable drive connected with the first piston rod, wherein the first piston rod is movable in both directions by the controllable drive; a shut-off valve; and a flushing gas feed opening into the feed line downstream from the three-way valve by way of the shut-off valve;
    (b) coupling the three-way valve, the controllable drive, and the shut-off valve with one another in such a manner that:
        in a first method step, the three-way valve releases a path of the sampling line to the at least one sample-taking cylinder, the shut-off valve is open, and the controllable drive pulls the sample-taking piston out of the at least one sample-taking cylinder for suction of the sample; and
        in a second method step, the shut-off valve is closed, the three-way valve is switched in such a manner that a path of the sample-taking piston to the feed line is released, and the controllable drive pushes the sample-taking piston again completely back into the at least one sample-taking cylinder for conveyance of the sample into the analytical evaluation system.

7. The method according to claim 6, wherein
    the controllable drive is configured as a piston/cylinder unit comprising a piston, a cylinder and a second piston rod connected with the first piston rod of the sample-taking piston, wherein the cylinder of the piston/cylinder unit has first and second pressure medium connectors on first and second sides of the piston, respectively, wherein each connector is connected with a pressure medium source by way of a common three-way valve.

8. The method according to claim 6, wherein the controllable drive is configured as a piston/cylinder unit comprising a piston and a cylinder and wherein the first piston rod serves as a common piston rod for the piston of the piston/cylinder unit and the sample-taking piston.

9. The method according to claim 6, wherein a plurality of sample-taking cylinders and a plurality of sample-taking pistons guided in the sample-taking cylinders are provided, wherein each sample-taking piston is connected with a separate fluid system and the feed line by way of a separate three-way valve.

10. The method according to claim 6, wherein the at least one sample-taking cylinder and the sample-taking piston guided in the at least one sample-taking cylinder are connected with a plurality of fluid systems and the feed line by way of a multi-way valve.

* * * * *